United States Patent [19]
Cross et al.

[11] Patent Number: 6,066,323
[45] Date of Patent: *May 23, 2000

[54] USE OF ANTIBODIES TO SIALIDASE AS ANTI-INFECTIOUS AGENTS AND ANTI-INFLAMMATORY AGENTS

[75] Inventors: Alan S. Cross, Chevy Chase, Md.; Nicholas Stamatos, Washington, D.C.; Peter Gomatos, Ft. Lauderdale, Fla.

[73] Assignee: The United States of America as represented by the Secretary of the Army, Washington, D.C.

[ * ] Notice: This patent is subject to a terminal disclaimer.

[21] Appl. No.: 08/736,236

[22] Filed: Oct. 23, 1996

Related U.S. Application Data

[63] Continuation-in-part of application No. 08/190,436, Feb. 2, 1994, Pat. No. 5,631,283.

[51] Int. Cl.$^7$ .................... A61K 39/395; C07K 16/40
[52] U.S. Cl. .................... 424/158.1; 424/146.1; 424/148.1; 424/160.1; 530/388.26; 530/389.1
[58] Field of Search ............. 424/146.1, 148.1, 424/160.1, 158.1; 514/459; 530/388.26, 389.1

[56] References Cited

U.S. PATENT DOCUMENTS 5,631,283   5/1997   Cross et al. .................... 514/459

OTHER PUBLICATIONS

Daar et al., *Proc. Natl. Acad. Sci. USA* 87:6574–6578, Sep. 1990.
Fahey et al., *Clin. Exp. Immunol.* 88:1–5, 1992.
Fox, J.L., *Bio/Technology*, 12:128, Feb. 1994.
Haynes et al., *Ann. Med.* 28:39–41, 1996.
Stamatos et al., *J. Cell. Biochem.* Suppl. 0 (16, Part E), p. 56, Abstract Q 348, Mar. 27, 1992.

*Primary Examiner*—Robert D. Budens
*Attorney, Agent, or Firm*—Charles H. Harris; John Francis Moran

[57] ABSTRACT

Sialic acids have the ability to prevent hyposialylation of cells as competitive inhibitors of endogenous sialidase. It is now also possible to develop antibodies to mammalian sialidase that significantly reduce influx of neutrophils into inflammatory sites.

4 Claims, No Drawings

USE OF ANTIBODIES TO SIALIDASE AS ANTI-INFECTIOUS AGENTS AND ANTI-INFLAMMATORY AGENTS

This application is a continuation-in-part of U.S. Ser. No. 08/190,436 filed Feb. 2, 1994, which has issued as U.S. Pat. No. 5,631,283.

FIELD OF THE INVENTION

This invention relates to the alteration of eukaryotic cell surfaces by administration of sialidase inhibitors (including antibodies to sialidase) or sialic acid.

BACKGROUND OF THE INVENTION

Part of the inflammatory process is accomplished by the circulating white blood cells, especially neutrophils, by (1) slowing down at a site within the blood vessel where an inflammatory response is developing, (2) adhering to the endothelial cells adjacent to the site of inflammation, (3) exiting the intravascular space through the lining of the blood vessels and (4) migrating to the inflammatory site within the tissues. In order to achieve this complex series of steps, the neutrophil must bind to the endothelial cells lining the vessels and then "unbind" so that it can continue on into the tissue. It is known that sialic acid residues on glycoconjugates of the cells are important to this initial binding.

The term "sialic acid" denotes members of a family comprising natural derivatives of neuraminic acid, an acid amino pyranose with 9 carbon atoms. In nature, the amino group is substituted either with an acetyl or glycolyl residue. The hydroxy groups may be methylated or esterified with groups such as acetyl, lactyl, sulfate, or phosphate groups. Multiple substitutions are common.

Sialic acids are a phylogenetically conserved family. These amino sugars are conjugated to protein and lipid moieties on the surface of mammalian cells and are potent modulators of biologic behavior. There is substantial evidence that sialic acids are structural determinants of important cell-to-cell interactions and cellular functions such as adhesiveness. There is considerable evidence that sialic acid residues protect molecules in circulation from recognition, clearance or degradation and that they regulate complement deposition on cell surfaces. Sialic acid residues also modulate attachment of microbial toxins as well as parasites to these cell surfaces.

The cleavage of the sialic acid by sialidases or neuraminidases from the glycoconjugates results in decreased rigidity of the cell surface, thereby facilitating cell motility, and effects cell-to-cell interactions such as adhesiveness and metastatic potential. Sialidases or neuraminidases are produced by many microbes and by mammalian cells. Whereas the presence of endogenous sialidase of mammalian cells has been well described, its role has best been studied primarily in a clinically heterogenous group of inherited disorders designated as sialidoses, wherein an abnormal amount of sialic acid accumulates in tissues of patients resulting in neurologic defects and premature death.

Endogenous sialidase in phagocytes has previously been described. It has been found that, upon activation such as may occur during infection or inflammation, this enzyme is translocated to the cell surface from sites within the cell (Cross and Wright, *Journal of Clinical Investigation. Inc.,* 88 (December, 1991) pp 2067–2076). The result of this mobilization is the removal of significant quantities of cell-associated sialic acid from glycoconjugates on cell surfaces. Desialylation of resting cells by microbial neuraminidase or of activated cells by mobilization of endogenous sialidases remove negative electric charges from cell surfaces and alters the biologic behavior of these cells to that typically observed during inflammation. Activation of cells in the presence of known sialidase inhibitors such as exogenous sialic acid prevents the desialylation and lowers cell adherence.

Interestingly, it has been shown that cell adherence is important in several infectious processes. Of greatest interest has been the effect of cell-to-cell transmission of human immunodeficiency virus (HIV). Infection of mammalian cells by HIV is known to be facilitated by activation of its cellular target.

The critical events in the multistep process of cellular activation that facilitates infection with HIV have not been identified. It has been shown that increased expression of endogenous sialidase follows activation of T lymphocytes by lectins and it has been suggested that this increase may play a role in the differentiation and maturation of these cells.

Specific inhibitors of sialidase activity have been used in vivo in mice to decrease mutual adhesion of blood platelets and to inhibit accumulation of leucocytes in microvascular beds that had been laser-irradiated. (Gorog, et al, *Br. J. exp. Path.* 61 (1980), 490).

Various sialidase inhibitors have previously been tested as treatment for influenza. Kumar, et al. (*Carbohydrate Research,* 94 (1981) 123–130) disclosed a method of synthesizing various neuraminic acids. Nohle, et al.(*J. Biochem,* 126 (1982) 543–548) discloses methods of synthesis of 2-deoxy-2,3-dehydro-N-acetyl-neuraminic acid and 2-deoxy-2,3-dehydroneuraminic acid and discusses the oral administration and secretion of the sialic acids. No method of using these inhibitors for anti-infective or anti-inflammatory use are taught therein. Nagai, et al. (*Biochemical and Biophysical Research Communications,* Vol 163, No. 1 (1989) and Miyaichi, et al. (*Shoyakugaku Zasshi,* 42 (3) (1988) 216–219) disclose use of a natural product from the leaf of *Scutellaria baicalensis* as an inhibitor of mouse liver sialidase, but its application to the treatment of inflammation is not discussed.

SUMMARY OF THE INVENTION

This invention relates to means of affecting disease conditions which are related to cell adherence by administration of sialic acid or of sialidase inhibitors. The active agents produce beneficial results by intervening in infectious processes in instances where pathogenicity of the disease-inducing organism is increased by microbial surface interaction with host cells.

The active agents described herein are also effective at inhibiting the activation of neutrophils which results in influx of the neutrophils into the tissues to cause inflammation. Hence, the methods described herein apply to amelioration of any conditions wherein increased cell adherence mediated resulting from sialidase increases morbidity, whether such morbidity is related to (1) cell-to-cell transfer of infectious organisms or (2) inflammatory processes.

Sialic acids may be delivered at dosage of 0.1 to 10 mg/kg intravenously 4–6 time a day. For humans, dosage forms would contain 5 to 1000 mg of sialic acid or sialic acid analogue.

Similar beneficial effects have now been obtained using IgG antibodies to sialidase administered at 0.1 to 30 mg/kg intravenously or to the target tissues.

DETAILED DESCRIPTION OF THE INVENTION

Sialic acids such as NANA have the ability to prevent hyposialylation of cells by competitive inhibition of the endogenous sialidase. The desialylation of cells is shown to increase adhesive properties of the cells and to render cells more susceptible to invasion by infectious organisms, particularly HIV. Cellular hyposialylation also accompanies inflammation. The sialidase inhibitors used as disclosed herein are effective in treating and/or in avoiding inflammation.

Sialic acid and its analogues are of the formula:

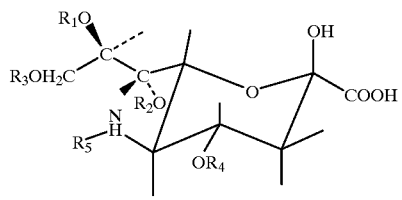

wherein $R_{1,2,3, \text{ and } 4}$ may be H, alkyl, $SO_3H$, $PO_3H_2$ or CO-alkyl, wherein alkyl has 1–4 carbons and may be substituted with OH and $R_5$ is CO-alkyl of 1–4 carbons which may be substituted with OH, with acetyl and glycolyl being preferred at $R_5$.

I. Inhibition of Cell-to-Cell Transmission of Infectious Organisms

Sialidase-treated peripheral blood mononuclear cells (PBMCs) support growth of HIV-1 in the absence of lectin activation. Treatment of PBMCs with sialidase or lectin (phytohemagglutinin) results in hyposialylation of the PBMC.

Materials and Methods:

Isolation and Culture of PBMCs:

Peripheral blood mononuclear cells were isolated from whole blood of HIV-1- and hepatitis B-seronegative donors by Ficoll-Paque (Pharmacia, Piscataway, N.J.) density gradient centrifugation and were grown in RPMI 1640 medium (GIBCO, Grand Island, N.Y.) containing 10% purified, delectinized human IL-2 (Advanced Biotechnologies, Inc., Columbia, Md.) and 15% heat-inactivated fetal bovine serum (GIBCO). Cells were maintained at 37° C. on $CO_2$-humidified incubator for 24 to 72 hours prior to treatment with phytohemagglutin (PHA) or neuraminidase, respectively.

Pretreatment of PBMCs with PHA or neuraminidase:

Cells at $10^7$ cells/ml were treated with PHA at 5 $\mu$g/ml for 30 minutes, were diluted 5-fold by addition of medium and were maintained in media containing PHA at 1 $\mu$g/ml. After 48 hours, cells were removed from the PHA-containing medium by centrifugation prior to infection with HIV-1. Alternatively, after 72 hours in culture, untreated cells were collected and resuspended at $10^7$ cells/ml for treatment at 37° C. for 30 minutes with 1 U/ml microbial neuraminidase, unless other treatment conditions were indicated. Cells were removed from the enzyme by centrifugation and were washed once prior to infection. Macrophage-depleted cultures were prepared for treatment with PHA or NANAse by collecting PBMCs which had not adhered to culture flasks after 24 or 72 hours, respectively. Cells exposed to PHA at 24 hours for stimulation during the subsequent 48 hours to provide 72 hours from seeding of cells to infection. Cells treated with sialidase were treated with enzyme 72 hours after seeding (immediately before infection). After 72 hours, PHA-or sialidase-(NANAse) treated cells were seeded in 96 well microtiter plates at $2.5\times10^5$ cells/well and were infected with HIV-1. Alternatively, infected cells were maintained in 75 cc flasks at $1\times10^5$ cells/ml.

HIV infection of PBMCs:

HTLV-IIIB/H9 strain HIV adapted to T cell lines were used to infect the PBMCs in the wells of microtiter plates at 50, 5, 1 or 0.5 $TCID_{50}$ of HIV-1 in final volume of 0.25 ml in media containing POLYBRENER (Sigma) at 1 $\mu$g/ml. (When infected cells were maintained in flasks, $0.8\times10^7$ cells were infected with $1.6\times10^3$, $1.6\times10^2$, and $1.6\times10$ $TCID_{50}$ in a volume of 2 ml for 2 hours at 37° C. to remove unadsorbed virus, cells were centrifuged, washed once, and seeded in 75 cc flasks at $1\times10^6$ cells/ml.) In both the microtiter plates and in the flasks, cells were incubated at 37° C. for 21 days. One half volume of media was removed. One day post infection and every 2 days thereafter to be replaced with an equal volume of fresh medium. Levels of p24 Ag in culture fluids were determined by ELISA (Coulter Immunology, Hialeah, Fla.).

Determination of total cell-associated sialic acid:

Cells treated with PHA, NANAse or untreated cells were washed three times in cold RPMI before exposure of pelletted cells to 0.1 M $H_2SO_4$ at 80° C. for one hour to release cell-associated sialic acid. Free sialic acid was measured by the Warren Assay.

Determination of cellular sialidase activity:

PBMCs in RPMI 1640 medium containing 10% fetal bovine serum and 4 U/ml of recombinant human IL-2 (Boehringer Mannheim, Indianapolis, Ind.) were incubated at 37° C. for 48 hours alone or with PHA (7.5 $\mu$g/ml). After 48 hours, cells were reisolated in a density gradient of Lymphocyte Separation Medium and were washed twice. After resuspension of cells in RPMI 1640 at $80\times10^6$ cells/ml, sialidase activity was assayed by incubating intact cells with neurminyl-lactose (Sigma) 1 mg/ml at 37° C. for 2 hours. Sialidase activity was determined by correlating the amount of sialic acid released from intact cells to a standard curve generated by determination of sialic acid released from neuraminyl lactose by 10 mU/ml NANAse.

Results:

Treatment of cells with sialidases rendered the peripheral blood mononuclear cells susceptible to infection with HIV, while administration of sialic acids counteracted the effects of sialidase. (See Table I.)

TABLE I

Susceptibility of pretreated PBMC's in neuraminidase and PHA:

| Experiment | HIV-1 inoculum ($TCID_{50}/2.5 \times 10^5$ cells) | p24 Ag(ηg/ml) released from cells pretreated with: None | PHA | NANAse |
|---|---|---|---|---|
| #1 | 50 | 32 | 73 | 41 |
| | 5 | 7 | 72 | 20 |
| | 1 | 0 | 69 | 26 |
| #2 | 59 | 12 | ND | 15 |
| | 5 | 0 | ND | 16 |
| | 0.5 | 0 | ND | 12 |
| #3 | 0.5 | 0 | 5 | 50 |

It has also been found that the effect of sialidases can be counteracted by administration of competitive inhibitors of sialidases, specifically by administration of analogues of sialic acid. Neuraminic acid (NeuAc) and 2,3-dehydro-2-desoxy-N-acetyl-neuraminic acid (NeuAc2en) were tested as competitive inhibitors of neuraminidases. Growth of HIV was not detected in cells which had been pretreated with NANAse in the presence of 250 $\mu$M NeuAc or NeuAc2en. Hence, presence of the competitive inhibitors of the NANAse protected cells from vulnerability to the HIV-1. (See Table II.)

TABLE II

Protective effect of sialic acid analogues on growth of HIV:

| Conditions of NANAse pretreatment of PBMC's | p24 Ag (ng/ml) released | |
|---|---|---|
| | day 12 | day 22 |
| 1 U/ml, 240 min | 54 | 56 |
| 1 U/ml, 30 min | 59 | 56 |
| 0.1 U/ml, 30 min | 0 | 0 |
| 1 U/ml + NeuAc (250 μM), 30 min | 0 | 0 |
| 1 U/ml + NeuAc2en (250 μM), 30 min | 0 | 0 |
| Heat-inactivated NANAse, 30 min | 0 | 0 |

Sialic acid analogues are effective at dosages of about 0.1 to 10 mg/Kg for 4 to 6 hours. Administration intravenously of the sialic acid analogue can be used to effectively protect cells from infection with HIV. By methods of the invention, the patient with HIV may be placed on a regimen to protect the cells through one replacement cycle for the PBMC's.

Synthesis of viral DNA is initiated following infection of both activated and quiescent primary lymphocytes, but HIV genomic RNA is not transcribed completely for full-length double-stranded DNA in quiescent PBMC. HIV can remain latent in quiescent cells for an extended period of time, but if mitogenic stimulation occurs within 4–8 days of infection, synthesis of viral DNA is completed and growth of virus occurs. Hence, administration of sialic acid analogues can be used to protect cells during early stages of infection (the period immediately after exposure to HIV) from completion of the viral growth cycle.

II. Modulation of Inflammatory Response

Materials and Methods:

The injection of thioglycollate into the peritoneum of animals is a well-established experimental technique for eliciting an inflammatory response. Therefore, mice were pre-treated intravenously with either a competitive inhibitor of sialidase (sialic acid was used) or with a polyclonal rabbit anti-sialidase antisera in an attempt to have inhibitors of sialidase circulating in the blood at the time of initiation of the inflammatory process with thioglycollate. It was reasoned that if these agents were effective in inhibiting sialidase and if sialidase were important in the inflammatory response, a decreased amount of cells migrating into the peritoneal site of inflammation would be seen. Preventive effects in mice:

Three groups of mice were studied for response to injections of thioglycollate in amounts sufficient to cause an inflammatory response. All groups were pretreated:

Group 1: Mice were pretreated intravenously with normal rabbit serum.

Group 2: Mice were pretreated intravenously with rabbit antisera containing increased levels of antibodies to sialidase.

Group 3: Mice were pretreated intravenously with sialic acid.

Results:

Mice in groups 2 and 3 showed less inflammatory response than was seen in the mice treated with normal rabbit serum. Hence, it was seen that both antibodies to sialidase and sialic acid showed anti-inflammatory effects.

III. Antibodies which Bind Sialidase:

It has now become possible to develop antibodies to mammalian sialidase that significantly reduce the influx of neutrophils into inflammatory sites. Since comparison of neuraminidase from different bacterial sources revealed conserved areas of homology, it was hypothesized that mammalian sialidase may have similar areas of homology with bacterial equivalents. Consequently, rabbits were immunized with Clostridia neuraminidase and the antibodies tested for binding activity against mouse and human sialidase.

Materials and Methods:

Preparation of antibodies:

New Zealand white rabbits were immunized with type V neuraminidase from *Clostridium perfringes.* After receiving a primary series of immunizations with adjuvant, rabbits received two booster doses before being bled. This antiserum was passed through a protein G Sapharose column and the adherent IgG was recovered following elution of the bound IgG by Tris-glycine buffer (at acid pH). The eluted IgG was returned to neutral pH by addition of sodium hydroxide. The recovered preparation had a protein concentration of 5.4 mg/ml. In order to test for its ability to bind to human sialidase by flow cytometry, the antibody was incubated at 4° C. for 15 minutes with the intact neutrophils that were either unstimulated (resting) or stimulated with formyl-methionyl-leucyl-phenylalanine (FMLP). (The neutrophils were previously incubated in immuno globulin for intravenous use (IVIG) to block non-specific binding of Fc receptors. Binding of the rabbit antisialidase was detected by fluorescein-conjugated goat anti-rabbit IgG. Analysis of binding by flow cytometry revealed the anti-neuraminidase bound only to the activated human neutrophils. This reaction indicates that this antibody preparation made with a bacterial antigen did, in fact, cross-react with components of human sialidase.

Animal models of Cytokine-induced Neutrophil Chemotaxis

Both models used in testing take advantage of the ability of interleukin 8 (IL-8) to attract neutrophils to inflammatory sites. This cytokine is induced after a wide variety of inflammatory stimuli. The production of this cytokine causes the recruitment of neutrophils to the site of the IL-8 production in a dose related manner. Neutrophils have cell surface receptors for IL-8 that allow them to respond to the presence of this molecule in the environment. In the absence of translocated sialidase, the neutrophil would be less capable of responding to the IL-8. This would be manifest as a reduction in the number of neutrophils at the site of IL-8 molecules.

Two models of IL-8-induced inflammation were employed. In the murine pneumonitis model, various concentrations of IL-8 were introduced into the nares of mice with the expectation some of the IL-8 would reach the murine lung. Within four hours of its introduction, there is a profuse neutrophil response that is evident both histologically upon counting the cells in the bronchoalveolar lavage (BAL) or upon measurement of total lung neutrophil content by the myeloperoxidase determination. At 24 hours after IL-8 instillation, there is a shift to a predominantly monocyte response.

In a second model of IL-8-induced inflammation (murine peritonitis model), IL-8 is given intraperitoneally. As is the case in the lungs, it is possible to follow the influx of neutrophils into this cavity by direct counts of cells harvested in peritoneal lavage. In this instance, there is a peak response of neutrophils at four hours.

Animal Models of Cytokine-induced Neutrophil Chemotaxis

Murine pneumonitis model: 25 gram mice which had been pretreated 1 hour previously with intravenous rabbit IgG or rabbit anti-neuraminidase antibody (20 mg/kg or 0.5 mg/25 gm mouse in 100 μl solution) were given either IL-8 (2.5 μg) or normal saline intra-nasally. The animals were sacrificed at four hours, a point previously established to be the time of maximal influx of neutrophils into the lung. The number of neutrophils in the lungs was assessed by an assay for myeloperoxidase. The animals that had been pretreated with the immune antibody had a decrease in the influx of neutrophils into the lung, whether the influx was imitated by saline or IL-8.

Murine peritonitis model: Pharmacologic inhibition of sialidase with the competitive inhibitor, sialic acid, was tested. Pretreatment of animals with sialic acid (10 mg/kg given intravenously) was followed after 5 minutes with the intraperitoneal administration of IL-8 (75 ηg). The influx was assessed by peritoneal lavage of mice and counting cells by hemocytometer. Pretreatment resulted in a highly significant decrease in number of neutrophils in the peritoneum. However, the decrease was short lived, since sialic acid is rapidly cleared from the bloodstream. The tests were repeated with multiple intravenous infusions of sialic acid (post-IL-8 5, 30, 60, 120, 180 and 210 minutes). The repeated infusions resulted in highly significant decrease in the entry of neutrophils into the peritoneum at 240 minutes post-L-8.

To prolong the activity of sialic acid, the molecule may be coupled to another carrier molecule such as polyethylene glycol or may be protected in liposomes, micro-crystals or microdroplets to provide prolonged activity.

Sialic acid and sialic acid analogues may be given intravenously or into the site of inflammation. For example, the active agents may be administered into, for example joints, the peritoneal cavity, the bowel or into the lung. Devices which produce mists may be used as appropriate.

In may instances, the effects of inflammation are as serious as the effects of infection. For example, inflammatory response to meningitis infection often causes death or chronic and severe central nervous system (CNS) impairment more severe than the deleterious effects of the infection. Sialic acid or sialic acid analogues or of antibodies to sialidase as disclosed herein could be administered by intrathecal route to protect from the pathological inflammation of the neuronal and epithelial tissue of the central nervous system. Examples of common carriers include isotonic saline, buffered saline and glucose in water or saline.

| | |
|---|---|
| Example: | |
| Composition for parenteral or topical use: | |
| Sialic acid | 10 mg |
| Phosphate buffered saline | 5 ml. |
| Example: | |
| Composition for parenteral use: | |
| Purified IgG antibodies to sialidase | 10 mg. |
| 10% glucose in ½ normal saline | 10 ml. |
| Example: | |
| Neuraminic acid | 10 mg. |
| ½ normal saline | 10 ml. |
| Example: | |
| 2,3-dehydro-2-desoxy-N-acetyl-neuraminic acid | 20 mg. |
| phosphate-buffered saline | 10 ml. |

All of the compositions may be provided as a sterile solutions in a single dose or multiple dose vial. The compositions may be administered parenterally or topically.

We claim:

1. A composition of matter comprising an inflammation-inhibiting effective amount of IgG antibody against a bacterial sialidase in a pharmaceutically acceptable carrier.

2. A method of treating or preventing inflammatory conditions comprising the administration of an anti-inflammatory effective amount of a composition of claim 1 in a pharmaceutically acceptable carrier.

3. A composition of matter comprising an amount of IgG antibody against a bacterial sialidase sufficient to inhibit invasion of peripheral mononuclear blood cells with HIV organisms in a pharmaceutically acceptable carrier.

4. A method of protecting blood mononuclear cells from invasion with HIV comprising administration of a composition containing an HIV infection-inhibiting effective amount of IgG antibody against a bacterial sialidase in a pharmaceutically acceptable carrier.

* * * * *